(12) United States Patent
Berglund

(10) Patent No.: US 6,234,182 B1
(45) Date of Patent: May 22, 2001

(54) PREFABRICATED DENTAL FLOSS DEVICE

(76) Inventor: Stig Olof Berglund, Johan Skyttes väg 240, S-125 34 Älvsjö (SE)

( * ) Notice: Subject to any disclaimer, the term of this patent is extended or adjusted under 35 U.S.C. 154(b) by 0 days.

(21) Appl. No.: 09/647,152

(22) PCT Filed: Mar. 26, 1999

(86) PCT No.: PCT/SE99/00481

§ 371 Date: Sep. 27, 2000

§ 102(e) Date: Sep. 27, 2000

(87) PCT Pub. No.: WO99/49806

PCT Pub. Date: Oct. 7, 1999

(30) Foreign Application Priority Data

Mar. 27, 1998 (SE) .................................................. 9801072

(51) Int. Cl.⁷ .................................................. A61C 15/00
(52) U.S. Cl. .......................................... 132/323; 132/328
(58) Field of Search ..................... 132/323, 324, 132/326, 327, 328, 329

(56) References Cited

U.S. PATENT DOCUMENTS 4,342,324 * 8/1982 Sanderson ............................ 132/324
4,403,625   9/1983 Sanders et al. ...................... 132/323
5,174,314  12/1992 Charatan ............................. 132/328
5,911,229 * 6/1999 Chodorow ............................ 132/323

* cited by examiner

Primary Examiner—John J. Wilson
Assistant Examiner—Melba Bumgarner
(74) Attorney, Agent, or Firm—Evenson, McKeown, Edwards & Lenahan, P.L.L.C.

(57) ABSTRACT

A prefabricated dental floss device comprises a dental floss holder (10), having the general shape of an elongate rod-like body and consisting of two interconnected but easily separable holder portions (12, 13), and a piece of dental floss (11), received in a cavity (15) in the dental floss holder (10) and anchored to the two holder portions (12, 13) with opposite end portions thereof and adapted to become uncovered along the major portion of its length when the holder portions (12, 13) are separated from each other. Said cavity is formed by a narrow groove (15), running in the longitudinal direction of the holder (10) and extending into the holder (10) from one side of the holder, said groove (15) containing the dental floss piece (11) within the same in a position adjacent to the bottom of said groove, the end portions of the dental floss piece (11) being permanently fixed to the holder (10) at places (16) located near mutually opposite ends of the holder.

15 Claims, 2 Drawing Sheets

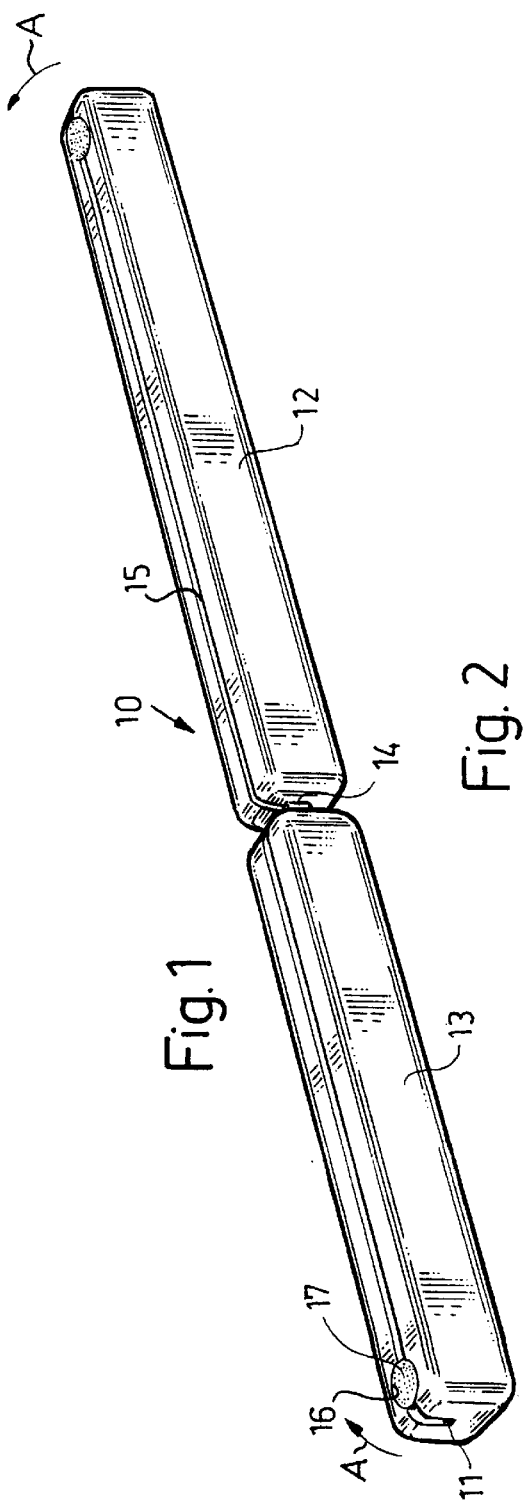
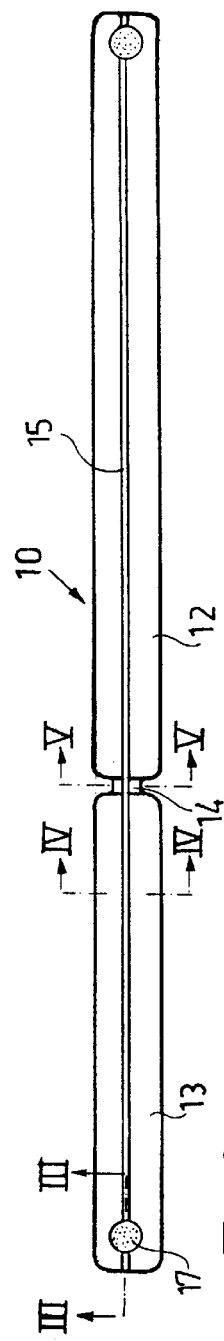
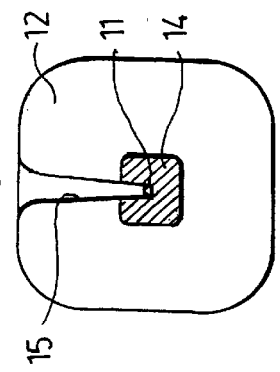
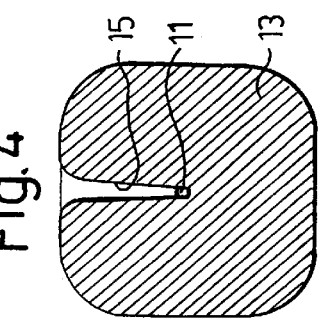
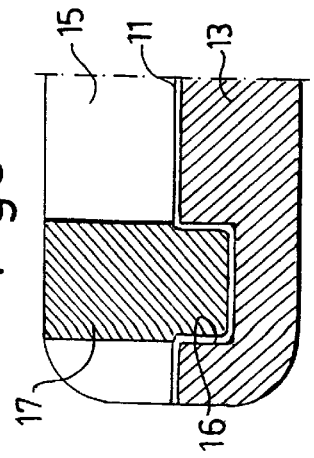

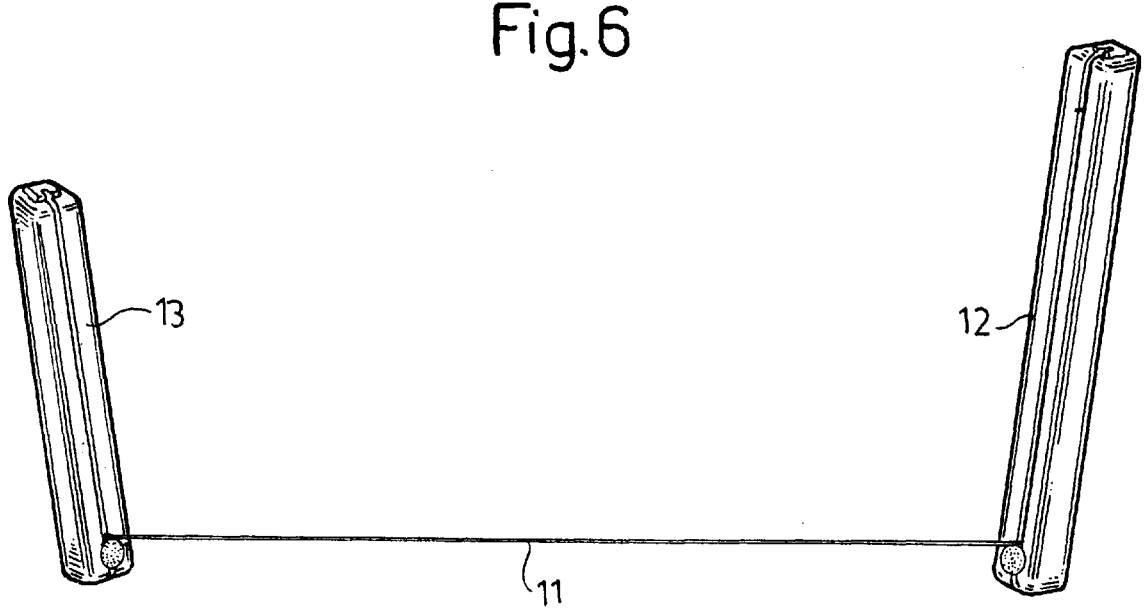

PREFABRICATED DENTAL FLOSS DEVICE

BACKGROUND AND SUMMARY OF THE INVENTION

The present invention relates to a prefabricated dental floss device.

Since long ago, it is well-known that the risk of the growth of bacteria on tooth surfaces, being difficult or impossible to clean by means of a tooth brush, may be effectively reduced by regular use of dental floss. However, the original classic manner of using dental floss, which is based on holding the dental floss manually by means of the fingers of both hands, is regarded as very troublesome and difficult by many people.

Therefore, in order to facilitate and promote the use of dental floss, various dental floss holders have been proposed. These holders may be divided into two different groups, namely on the one hand, a first group of holders, intended for repeated use and based on the assumption that a user affixes a fresh piece of dental floss to the holder each time he is going to use the holder, and, on the other hand, a second group of holders which are provided with dental floss pieces previously affixed thereto and which together with said dental floss pieces form prefabricated dental floss devices intended for single use.

In both cases, the holders have usually had a york of fork-like shape and been provided with two legs which are rigidly connected to each other and between which the dental floss is mounted in a taut state. However, such a mounting of the dental floss does not permit the dental floss to be wrapped around a tooth and brought to follow the contour of the tooth. Therefore, the possible cleaning of the teeth is strongly restricted. Furthermore, it may very well happen that the dental floss, taut between the two legs, will cut into raised portions of the gumline and hereby cause injuries on the latter.

In order to avoid the above disadvantages and make it possible to achieve a cleaning effect which is just as good as in the case of the classic entirely manual procedure without having to put fingers of both hands into the mouth, also various prefabricated dental floss devices intended for single use have been proposed, comprising a dental floss holder, having the general shape of an elongate rod-like body and consisting of two interconnected but easily separable holder portions, and a piece of dental floss, received in a cavity in the dental floss holder and anchored to the two holder portions with opposite ends thereof and adapted to become uncovered along the major portion of its length when the holder portions are separated from each other. However, despite the obvious advantages offered by dental floss devices of this kind, any such devices have not found any substantial use in practice. No doubt, the reason is that the devices hitherto proposed, for instance those dislosed in U.S. Pat. No. 4,403,625 and U.S. Pat. No. 5,174,314, have not been designed in a manner that could be accepted when considering the required manufacturing process.

The invention has for its purpose to provide an improved dental floss device of said kind which can be produced in a much more simple and inexpensive manner than the devices previously known.

The device, according to the invention proposed for said purpose, is primarily characterized in that said cavity in the dental floss holder is formed by a narrow groove, running in the longitudinal direction of the holder and extending into the holder from one side of the holder, said groove containing the dental floss piece within the same in a position adjacent to the bottom of said groove, the end portions of the dental floss piece being permanently fixed to the holder at places located near mutually opposite ends of the holder.

As a consequence of the design of the dental floss device proposed in accordance with the invention, the manufacture of the dental floss holder as well as the fixation of the dental floss piece to said holder may be effected in an easy and inexpensive manner.

According to a preferred embodiment of the invention, the dental floss holder may suitably be formed by an injection moulded integral member which consists of a rigid plastic material and wherein the two holder portions are connected to each other by a weakened easily breakable connection portion.

The dental floss holder may advantageously consist of a styrene acrylonitrile plastic.

In order to facilitate a convenient and firm holding of each of the two holder portions by a user, said portions may preferably have a non-circular cross-sectional shape. For instance, the two holder portions may advantageously have a cross-sectional shape consisting of a square or a rectangle with rounded corners.

The two end portions of the dental floss piece, which suitably may consist of a multifilament thread consisting of a polyamide plastic, may be fixed to the dental floss holder in many different ways. For instance, they may be fixed to the holder each by means of a plug, inserted into and secured in a bottom hole in the corresponding holder portion. However, they may preferably be fixed to the holder by glue joints or melt joints.

BRIEF DESCRIPTION OF THE DRAWINGS

Below the invention is described in further detail with reference to the accompanying drawings, in which FIG. 1 shows a perspective view of a prefabricated dental floss device according to an embodiment of the invention, selected by way of example only, FIG. 2 shows a plan view of the dental floss device according to FIG. 1, FIG. 3 shows a partial view on an enlarged scale and in section taken along line III—III in FIG. 2, FIG. 4 shows a cross-sectional view, taken along line IV—IV in FIG. 2, FIG. 5 shows a cross-sectional view, taken along line V—V in FIG. 2, and FIG. 6 shows a perspective view of the device according to FIG. 1 after a separation of two holder portions of said device from each other.

DETAILED DESCRIPTION OF THE DRAWINGS

The dental floss device shown in the drawings comprises a dental floss holder, generally designated 10, and a piece of dental floss 11, fixed to said holder.

As a whole, holder 10 has a generally rod-like shape and it consists of two holder portions 12 and 13, respectively, which are located in line with each other and each of which as a cross-sectional shape consisting of a square or rectangle with rounded corners. At their adjacent ends, the two holder portions 12 and 13 are connected to each other by a short connection portion 14, the cross-section of which is strongly reduced in relation to the cross-section of said two portions.

At one side thereof, holder 10 is provided with a narrow groove 15, running along the whole length of the holder and extending into the centre of the holder from said one side thereof and serving to receive dental floss piece 11 in a position located at the bottom of said groove. Dental floss piece 11, which extends along the whole length of holder 10, is permanently fixed to each holder portion 12 and 13, respectively, at a place located near the outer end of the holder portion. In the drawings, said fixation of the dental floss piece to each holder portion has been illustrated as obtained by means of a generally cylindrical plug 17, inserted into and secured in a bottom hole 16 in the holder portion. However, said fixation may be obtained also in many other ways. Thus, in practice, the end portions of dental floss piece 11 may preferably be fixed to the holder portions by glue joints or melt joints.

Holder 10 may preferably consist of an injection moulded integral member consisting of a rigid plastic material. In this case, connection portion 14 may serve as an easily breakable weakened connection between the two holder portions 12 and 13, while each holder portion simultaneously may form a rigid elongate generally rod-like member. One suitable material for the production of holder 10 is styrene acrylonitrile plastic.

The dental floss piece 11 may suitably consist of a multifilament thread of a polyamide plastic.

When the dental floss device above described is to be used, dental floss piece 11, which previously has been located protected in groove 15, may be uncovered by swinging the outer ends of holder portions 12 and 13 towards each other in a manner indicated by. arrows A in FIG. 1. Hereby, connection portion 14 is broken and the two holder portions 12 and 13 are separated from each other so as to form two separated members which may be handled individually and which are connected each to one end portion of dental floss piece 11. The user may then conveniently handle dental floss 11 in any desired manner while holding the two holder portions 12 and 13 in different hands.

In order to make it possible for a user to put the end of the dental floss connected to one holder portion into a lingual position in his mouth without simultaneously having to put the fingers by which he is holding said holder portion into a corresponding position, the holder portion should have a length of at least about 3 centimetres. However, a larger length may be advantageous. If, as shown in the drawings, the two holder portions have mutually different lengths, the shorter holder portion may suitably have a length of at least 3 centimetres and preferably 3,5–4 centimetres, while the longer holder portion may have a length of at least 4 centimetres and preferably 5–6 centimetres.

The cross-sectional dimensions of the two holder portions should amount to at least about 3 millimetres but may just as well be slightly larger, for instance about 4 millimetres.

The invention is not restricted to the embodiment above described and shown in the drawings. Instead, many other embodiments are feasible within the scope of the invention. For instance, it could be mentioned that the two holder portions need not have the shape of absolutely straight rod-like members but may also consist of suitably curved such members.

What is claimed is:

1. Prefabricated dental floss device, comprising a dental floss holder (10), having the general shape of an elongate rod-like body and consisting of two interconnected but easily separable holder portions (12, 13), and a piece of dental floss (11), received in a cavity (15) in the dental floss holder (10) and anchored to the two holder portions (12, 13) with opposite end portions thereof and adapted to become uncovered along the major portion of its length when the holder portions (12, 13) are separated from each other, characterized in that said cavity in the dental floss holder (10) is formed by a narrow groove (15), running in the longitudinal direction of the holder (10) and extending into the holder (10) from one side of the holder, said groove (15) containing the dental floss piece (11) within the same in a position adjacent to the bottom of said groove, the end portions of the dental floss piece (11) being permanently fixed to the holder (10) at places (16) located near mutually opposite ends of the holder.

2. A device according to claim 1, characterized in that the dental floss holder (10) is formed by an injection moulded integral member which consists of a rigid plastic material and wherein the two holder portions (12, 13) are connected to each other by a weakened easily breakable connection portion (14).

3. A device according to claim 2, characterized in that the dental floss holder (10) consists of a styrene acrylonitrile plastic.

4. A device according to claim 3, characterized in that the two holder portions (12, 13) have a non-circular cross-sectional shape.

5. A device according to claim 3, characterized in that the end portions of the dental floss piece (11) are fixed to the holder (10) each by means of a plug (17), inserted into and secured in a bottom hole (16) in the corresponding holder portion.

6. A device according to claim 3, characterized in that the end portions of the dental floss piece (11) are fixed to the holder (10) by glue joints or melt joints.

7. A device according to claim 2, characterized in that the two holder portions (12, 13) have a non-circular cross-sectional shape.

8. A device according to claim 2, characterized in that the end portions of the dental floss piece (11) are fixed to the holder (10) each by means of a plug (17), inserted into and secured in a bottom hole (16) in the corresponding holder portion.

9. A device according to claim 2, characterized in that the end portions of the dental floss piece (11) are fixed to the holder (10) by glue joints or melt joints.

10. A device according to claim 1, characterized in that the two holder portions (12, 13) have a non-circular cross-sectional shape.

11. A device according to claim 10, characterized in that the two holder portions (12, 13) have a cross-sectional shape consisting of a square or rectangle with rounded corners.

12. A device according to claim 10, characterized in that the end portions of the dental floss piece (11) are fixed to the holder (10) each by means of a plug (17), inserted into and secured in a bottom hole (16) in the corresponding holder portion.

13. A device according to claim 10, characterized in that the end portions of the dental floss piece (11) are fixed to the holder (10) by glue joints or melt joints.

14. A device according to claim 1, characterized in that the end portions of the dental floss piece (11) are fixed to the holder (10) each by means of a plug (17), inserted into and secured in a bottom hole (16) in the corresponding holder portion.

15. A device according to claim 1, characterized in that the end portions of the dental floss piece (11) are fixed to the holder (10) by glue joints or melt joints.

\* \* \* \* \*